United States Patent
Cureton et al.

(10) Patent No.: US 9,795,516 B2
(45) Date of Patent: *Oct. 24, 2017

(54) WOUND DRESSING GARMENT

(71) Applicant: ROAR CONSULTANTS, Naples, FL (US)

(72) Inventors: Mary Rose Cureton, Naples, FL (US); Michael J. Kane, Mountaintop, PA (US)

(73) Assignee: ROAR CONSULTANTS, Naples, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 15/013,442

(22) Filed: Feb. 2, 2016

(65) Prior Publication Data

US 2016/0143787 A1 May 26, 2016

Related U.S. Application Data

(63) Continuation of application No. 13/649,981, filed on Oct. 11, 2012, now Pat. No. 9,248,050.

(Continued)

(51) Int. Cl.
*A61F 13/00* (2006.01)
*A61F 13/06* (2006.01)
(Continued)

(52) U.S. Cl.
CPC ........ *A61F 13/06* (2013.01); *A61F 13/00017* (2013.01); *A61F 13/00021* (2013.01);
(Continued)

(58) Field of Classification Search
None
See application file for complete search history.

(56) References Cited

U.S. PATENT DOCUMENTS 3,249,109 A 5/1966 Maeth et al.
3,648,291 A 3/1972 Pankers
(Continued)

FOREIGN PATENT DOCUMENTS

GB 1049196 11/1966
GB 2465350 A 5/2010
(Continued)

OTHER PUBLICATIONS

Convatec, "Aquacel Dressings Datacard", 4 pages, http://www.dressings.org/Dressings/aquacel.html, retrieved online Dec. 5, 2012.

(Continued)

*Primary Examiner* — Kim M Lewis
(74) *Attorney, Agent, or Firm* — Birch, Stewart, Kolasch & Birch, LLP

(57) ABSTRACT

A wound dressing garment is provided. The wound dressing garment includes a wearable garment including a portion having a hole configured to receive a wound dressing therein in combination with the wound dressing. The wound dressing includes a border connecting the wound dressing to the wearable garment where the border extends around the perimeter of the hole to locate the wound dressing therein. The wound dressing may include one or more additional layers including a hydrogel layer. A method for treating wound or preventing bed sores using the wound dressing garment is also provided.

15 Claims, 9 Drawing Sheets

Related U.S. Application Data

(60) Provisional application No. 61/546,272, filed on Oct. 12, 2011.

(51) Int. Cl.
    *A61F 13/10* (2006.01)
    *A61F 15/00* (2006.01)
    *A61F 13/02* (2006.01)

(52) U.S. Cl.
    CPC .. *A61F 13/00029* (2013.01); *A61F 13/00046* (2013.01); *A61F 13/00051* (2013.01); *A61F 13/00085* (2013.01); *A61F 13/0213* (2013.01); *A61F 13/062* (2013.01); *A61F 13/064* (2013.01); *A61F 13/066* (2013.01); *A61F 13/067* (2013.01); *A61F 13/069* (2013.01); *A61F 13/101* (2013.01); *A61F 15/004* (2013.01); *A61F 2013/0054* (2013.01); *A61F 2013/0057* (2013.01); *A61F 2013/0091* (2013.01); *A61F 2013/00119* (2013.01); *A61F 2013/00127* (2013.01); *A61F 2013/00182* (2013.01); *A61F 2013/00246* (2013.01); *A61F 2013/00285* (2013.01); *A61F 2013/00404* (2013.01); *A61F 2013/00523* (2013.01); *A61F 2013/00557* (2013.01); *A61F 2013/00604* (2013.01); *A61F 2013/00748* (2013.01); *A61F 2013/00846* (2013.01); *A61F 2013/00855* (2013.01)

(56) References Cited

U.S. PATENT DOCUMENTS

| | | |
|---|---|---|
| 3,937,218 A | 2/1976 | Gaylord, Jr. |
| 4,150,442 A | 4/1979 | Boone |
| 4,153,055 A | 5/1979 | Etes |
| 4,166,463 A | 9/1979 | Bloom |
| 4,347,841 A | 9/1982 | Benyo et al. |
| 4,367,732 A | 1/1983 | Poulsen et al. |
| 4,438,258 A | 3/1984 | Graham |
| 4,516,571 A | 5/1985 | Buchan |
| 4,541,426 A | 9/1985 | Webster |
| 4,552,138 A | 11/1985 | Hofeditz et al. |
| 4,556,056 A | 12/1985 | Fischer et al. |
| 4,759,354 A | 7/1988 | Quarfoot |
| 4,846,164 A | 7/1989 | Martz |
| 4,909,244 A | 3/1990 | Quarfoot et al. |
| 4,917,112 A | 4/1990 | Kalt |
| 5,005,567 A | 4/1991 | Gilman et al. |
| 5,115,801 A | 5/1992 | Cartmell et al. |
| 5,160,328 A | 11/1992 | Cartmell et al. |
| 5,423,737 A | 6/1995 | Cartmell et al. |
| 5,497,513 A | 3/1996 | Arabeyre et al. |
| 5,593,395 A | 1/1997 | Martz |
| 5,682,617 A | 11/1997 | Tumas |
| 5,882,324 A | 3/1999 | Baranowski |
| 5,944,683 A | 8/1999 | Baranowski |
| 6,123,681 A | 9/2000 | Brown, III |
| 6,371,933 B1 | 4/2002 | Gardon-Mollard |
| 6,523,729 B1 | 2/2003 | Gardon-Mollard |
| 6,548,728 B1 | 4/2003 | Faries, Jr. et al. |
| 6,572,574 B2 | 6/2003 | Gardon-Mollard |
| 6,684,412 B2 | 2/2004 | Ricci et al. |
| D503,982 S | 4/2005 | Liedtke et al. |
| 7,091,394 B2 | 8/2006 | Kolte et al. |
| D537,948 S | 3/2007 | Smith |
| 7,213,420 B2 | 5/2007 | Lynch et al. |
| 7,345,215 B2 | 3/2008 | Fernfors et al. |
| 7,485,111 B1 | 2/2009 | Choi et al. |
| D620,122 S | 7/2010 | Cotton |
| 7,775,069 B1 | 8/2010 | Hermanson et al. |
| 7,896,823 B2 | 3/2011 | Mangrum et al. |
| 8,591,447 B2 | 11/2013 | DiGrazia |
| 9,248,050 B2 * | 2/2016 | Cureton ............ A61F 13/00051 |
| 2002/0062511 A1 | 5/2002 | Lee |
| 2003/0153860 A1 | 8/2003 | Nielsen et al. |
| 2003/0216676 A1 | 11/2003 | Gardon-Mollard |
| 2006/0010574 A1 | 1/2006 | Linnane et al. |
| 2006/0116622 A1 | 6/2006 | Pike |
| 2008/0071204 A1 | 3/2008 | Linnane et al. |
| 2008/0262403 A1 | 10/2008 | Martin |
| 2009/0148394 A1 | 6/2009 | Munro |
| 2010/0056971 A1 | 3/2010 | Quinon |
| 2011/0202018 A1 | 8/2011 | Dias et al. |

FOREIGN PATENT DOCUMENTS

| | | |
|---|---|---|
| WO | WO 02/102425 A2 | 12/2002 |
| WO | WO 2007/018484 A1 | 2/2007 |
| WO | WO 2009/156674 A1 | 12/2009 |
| WO | WO 2011/025396 A1 | 3/2011 |

OTHER PUBLICATIONS

Smith & Nephew Healthcare Limited, "Intrasite Gel Dressings Datacard", 3 pages, http://www.dressings.org/Dressings/intrasit.gel.html, retrieved online Dec. 5, 2012.

* cited by examiner

WOUND DRESSING GARMENT

CROSS-REFERENCE TO RELATED APPLICATIONS

This application is a Continuation of U.S. application Ser. No. 13/649,981, filed Oct. 11, 2012, which claims the benefit of U.S. Provisional Application No. 61/546,272, filed Oct. 12, 2011, which are herein incorporated by reference in their entireties.

BACKGROUND OF THE INVENTION

1. Field of the Invention

The present invention relates generally to a wound dressing incorporated into a garment for covering wounds on human and animal skin or to prevent wounds from developing on human and animal skin. More particularly, the present invention relates to a moisture vapor permeable dressing that is affixed or otherwise attached to a garment to facilitate manipulation of the dressing over the wound area.

2. Description of Related Art

Bed sores/pressure ulcers are pressure injuries that are just one type of trauma that can occur to skin. Generally it occurs from constantly lying in one position that prevents blood flow to particular tissue. As a result, the epidermis breaks down and then the dermis sloughs or shears off resulting in a shallow or deep wound.

Current approaches to treating these pressure injuries include foam based products, socks infused with gel using aloe or lanolin, or Latex products. However, foam based products tend to be bulky and add heat to the wound area inhibiting healing, socks infused with gel are non-therapeutic, and Latex applications have limited breathability.

In addition, most current wound care treatments include individual dressing pieces that imperfectly cover the wound. In fact, certain wound care treatments require cutting and applying customized dressing pieces which can be time consuming and makes rapid application of the dressing virtually impossible. Further, these cumbersome operations would have to be performed each time the dressing is changed.

For patients that are bed ridden, or are required to spend extended periods of time in bed, it is often difficult for them to spend the time in a single position whether it is on their side, prone or supine. As a result, there is often a need for constant repositioning of the wound dressing as patients shift about.

Therefore it is desirable to provide a wound dressing garment that addresses one or more of the problems identified above. As such, there is a need for a conformable wound dressing with high absorbency and an ability to fit different wound sites including the heel, elbow or other protuberances of a body without wrinkling or appearing bulky. In addition, the wound dressing garment should be useable with both bed ridden or ambulatory patients that allows treatment and monitoring of the wound. In addition to protecting and providing healing to wounds on the skin, there is a need to provide a system of preventing ulcers from forming, in particular to prevent the heels and elbows of patients at risk from ulcerating. In some instances it is also desirable to provide a wound dressing garment that allows for monitoring by a healthcare professional or individual.

BRIEF SUMMARY OF THE INVENTION

According to principles of this invention and to address one or more of the problems with conventional wound care treatments, a wound dressing garment is provided. The wound dressing garment includes a wearable garment including a portion having a hole configured to receive a wound dressing therein in combination with the wound dressing. The wound dressing includes a border connecting the wound dressing to the wearable garment where the border extends around the perimeter of the hole to locate the wound dressing therein.

The border may have a central opening and the wound dressing may include a hydrogel layer located at the central opening.

The wound dressing may include a mesh layer disposed below the hydrogel layer where the mesh layer is configured to allow dispersal of the hydrogel layer.

The wound dressing may further include an adhesive layer to secure the mesh layer to the hydrogel layer and the border.

The wound dressing may include at least one transparent layer above the hydrogel layer. The at least one transparent layer may be formed of one of a hypoallergenic film, an oxygen-permeable film and a vapor-permeable film. By way of example, the at least one transparent layer may include a first transparent layer formed of a hypoallergenic film and a second transparent layer formed of an oxygen-permeable, vapor-permeable film.

The wound dressing may include a structural layer disposed above the hydrogel layer where the structural layer and the adhesive layer prevent dispersion of the hydrogel layer prior to being placed on a body part.

The wearable garment may be selected from one of a sock and a sleeve. For example, the wearable garment may be a sock configured to be worn on a foot and the wound dressing may be located in one of a heel region, an ankle region, and a leg region of the sock. Alternatively, the wearable garment may be a sleeve configured to be worn on an appendage and the wound dressing is locatable to cover a joint of the appendage.

In accordance with the principles of the present invention, a wound dressing garment for treatment of wounds to skin or to protect the skin from wound development is provided. The wound dressing garment includes a wearable garment in the form of a sock or sleeve, the wearable garment having a hole configured to receive a wound dressing therein, the wearable garment being configured to hold the wound dressing in contact with the skin. The wound dressing may be configured to cover the skin to treat a wound or to protect the skin from developing a wound at the location of the wound dressing. The wound dressing includes a border connecting the wound dressing to the wearable garment where the border extends around the perimeter of the hole to locate the wound dressing therein. The border has a central opening. The wound dressing includes a hydrogel layer located at the central opening, a mesh layer disposed below the hydrogel layer, the mesh layer configured to allow dispersal of the hydrogel layer, an adhesive layer to secure the mesh layer to the hydrogel layer and the border, a structural layer disposed above the hydrogel layer, the structural layer and adhesive layer preventing dispersion of the hydrogel layer prior to contact with the skin and at least one transparent layer above the hydrogel layer.

The wearable garment may be provided with at least one of a ventilation channel tab, an evaporation channel and a resealable opening.

The wearable garment may be in the form of a sock and have an elastic cuff and a non-cinching portion. Alternatively, the wearable garment may be a sleeve having a pair of elastic cuffs.

The hydrogel layer may include hydrogel in combination with antibiotics or anti-inflammatories to assist in the treatment of a wound.

In accordance with principles of the present invention, a method of treating a wound on skin or preventing wound formation on skin is provided. The method includes placing a wound dressing garment described above on a foot or appendage and activating the wound dressing to cause dispersal of the hydrogel layer to the skin.

The method may further include monitoring the wound dressing, which may include observing the skin through the wound dressing.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The present invention will become more fully understood from the detailed description given hereinbelow and the accompanying drawings which are given by way of illustration only, and thus are not limitative of the present invention and wherein.

DETAILED DESCRIPTION OF THE INVENTION

Exemplary wound dressing garments will now be described with reference to the accompanying drawings. Like numbers referring to similar elements in the various exemplary embodiments will be used in the description that follows and the descriptions may not be repeated.

Figure 1:
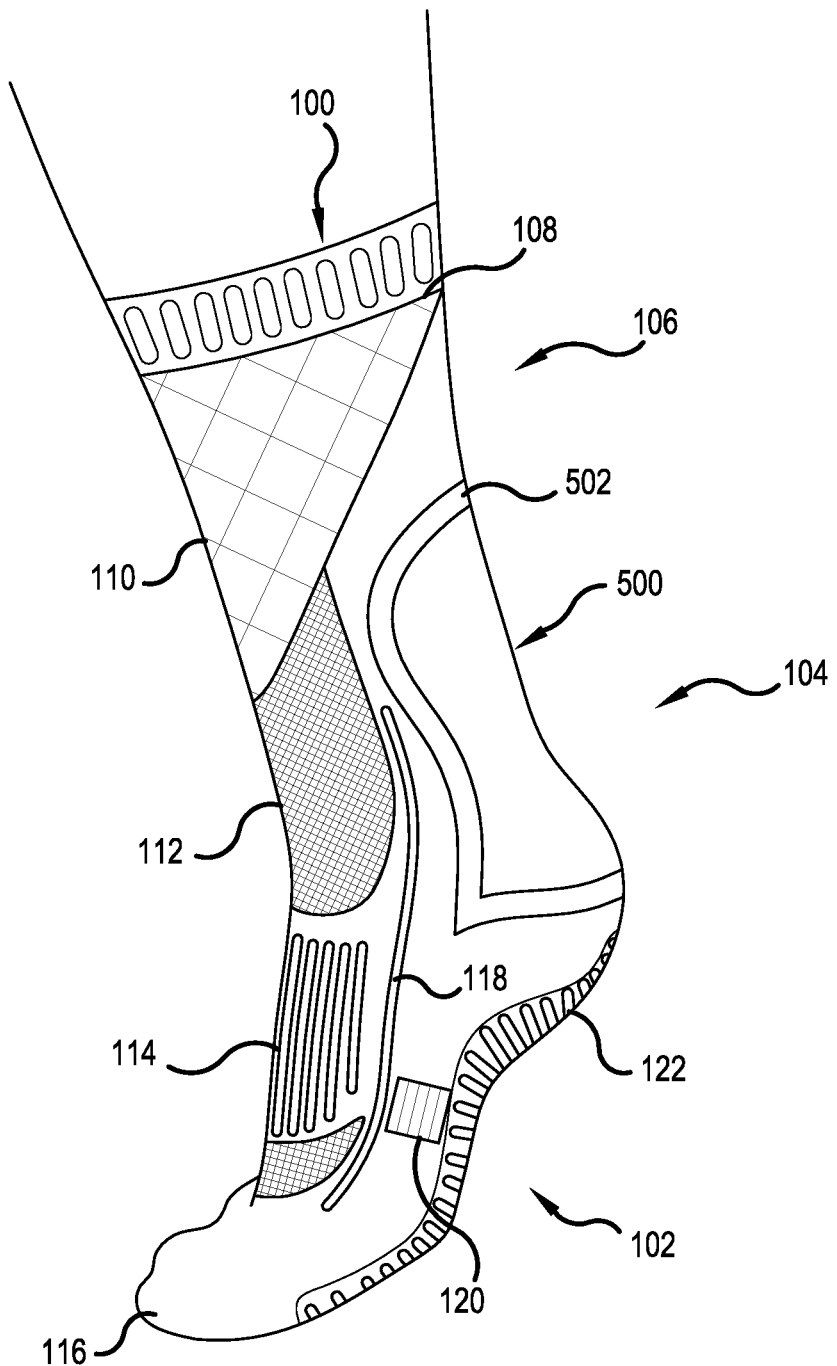
FIG. 1 illustrates a front perspective view of a wound dressing garment according to a first exemplary embodiment of the present invention and FIG. 1A illustrates a modification of the wound dressing garment of FIG. 1.

A wound dressing garment according to a first exemplary embodiment is illustrated in FIG. 1. The wound dressing garment includes a sock shaped garment 100, hereinafter "sock", and a wound dressing 500 affixed or attached thereto. The sock 100 is shaped so as to cover the foot and at least part of the calf of an individual. The sock 100 includes a foot portion 102, an ankle portion 104 and a leg portion 106. As shown in this exemplary embodiment, the wound dressing 500 may extend across the ankle portion 104 and the leg portion 106; however, it is understood that the wound dressing 500 is not limited to this location. For example, the wound dressing 500 may cover the rim of the heel edge extending to the sole. The wound dressing 500 includes a wound dressing border 502 that connects the wound dressing 500 to the sock 100. The wound dressing 500 will be discussed in greater detail below with respect to FIG. 6.

Figure 1A:
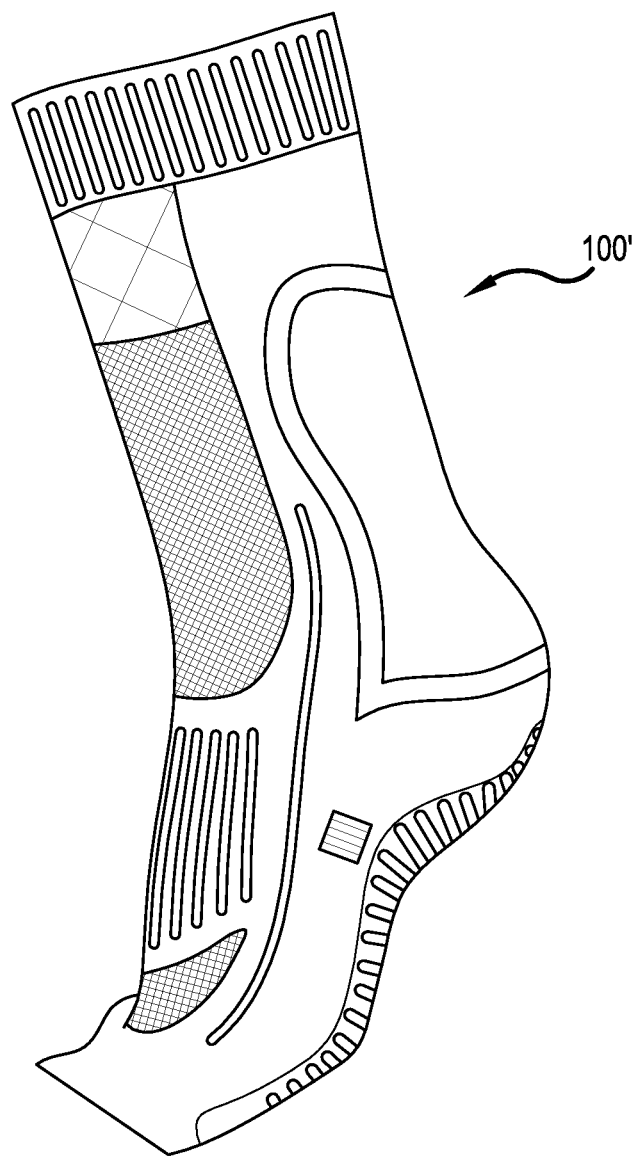

The sock 100 may include a non-binding, non-restrictive elastic cuff 108 provided at the top of the leg portion 106. The cuff 108 serves to prevent the sock from slipping down the leg of the individual. The cuff 108 may be attached to a large gauge mesh weave 110 that defines the upper portion of leg portion 106 and is stretchable to allow a foot to be inserted through the opening of the sock 100 and to contract and collapse against the leg of the individual once the foot is inserted. A smaller gauge mesh weave 112 is connected to the mesh weave 110 and spans the leg portion and the ankle portion. The mesh weave 112 may be in the form of a panel so as to cover the dorsum of the foot and may extend upward to cover a lower portion of the shin bone as it tapers and is joined to the mesh weave 110. A non-wrinkle or non-cinching portion 114 may be provided in the middle of the mesh weave 112 or it can be provided at one end of the mesh weave 112 opposite the mesh weave 110. As shown in FIG. 1, the non-wrinkle portion 114 may have a transition portion that tapers into a mesh weave prior to reaching a toe portion 116; however, it is understood that the non-wrinkle portion 114 may extend to the toe portion 116. The sock 100 ends at the toe portion 116 and the toe portion 116 may be designed to provide a wide or loose fit so as to not feel restrictive on a foot of the individual. To this end, the toe portion 116 may be seamless. Alternatively, the toe portion 116 may be eliminated, thereby providing an open-toe sock 100' arrangement as shown in FIG. 1A, so as to be less restrictive on the individual's foot.

The sock 100 may include a pair of evaporation channels 118 that extend along the sides of the sock from the toe portion 116 of the foot portion 102 towards the ankle portion 104. In addition, a pair of ventilation channel tabs 120, one for each side of the foot, may be disposed in the foot portion 102. The purpose of the evaporation channels 118 and ventilation channel tabs 120 is to allow for the evaporation and/or transportation of moisture.

A non-skid tread 122 may also be provided on the sole of the sock 100 in the foot portion 102. In the exemplary embodiment, the tread 122 extends between the ball of the foot and the heel of the foot; however, it is understood that the non-skid tread 122 may be provided at other portions of the sock. The tread 122 may be made of silicon rubber or other suitable materials.

To use the wound dressing garment, a health care professional or the individual can apply the sock 100 by placing it over the foot and leg. Once in place, the wound dressing garment is arranged so that the wound dressing 500 covers the heel, ankle, leg or portions thereof to cover any wounds, such as cuts, bruises or ulcers or to prevent ulcers from forming in that area. The health care professional or individual can adjust the location of the wound dressing to cover a majority of wounds that could occur in the heel, ankle or leg.

Figure 2:
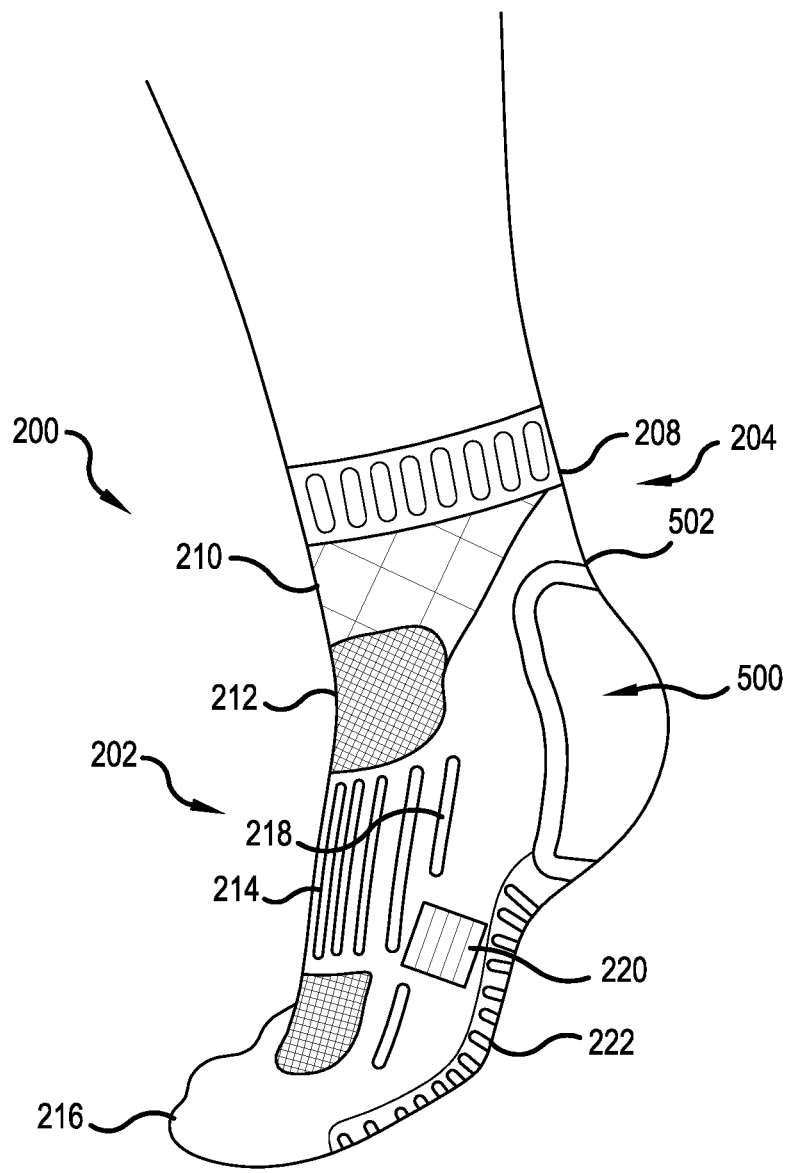
FIG. 2 illustrates a front perspective view of a wound dressing garment according to a second exemplary embodiment of the present invention and FIG. 2A illustrates a modification of the wound dressing garment of FIG. 2.
Figure 3:
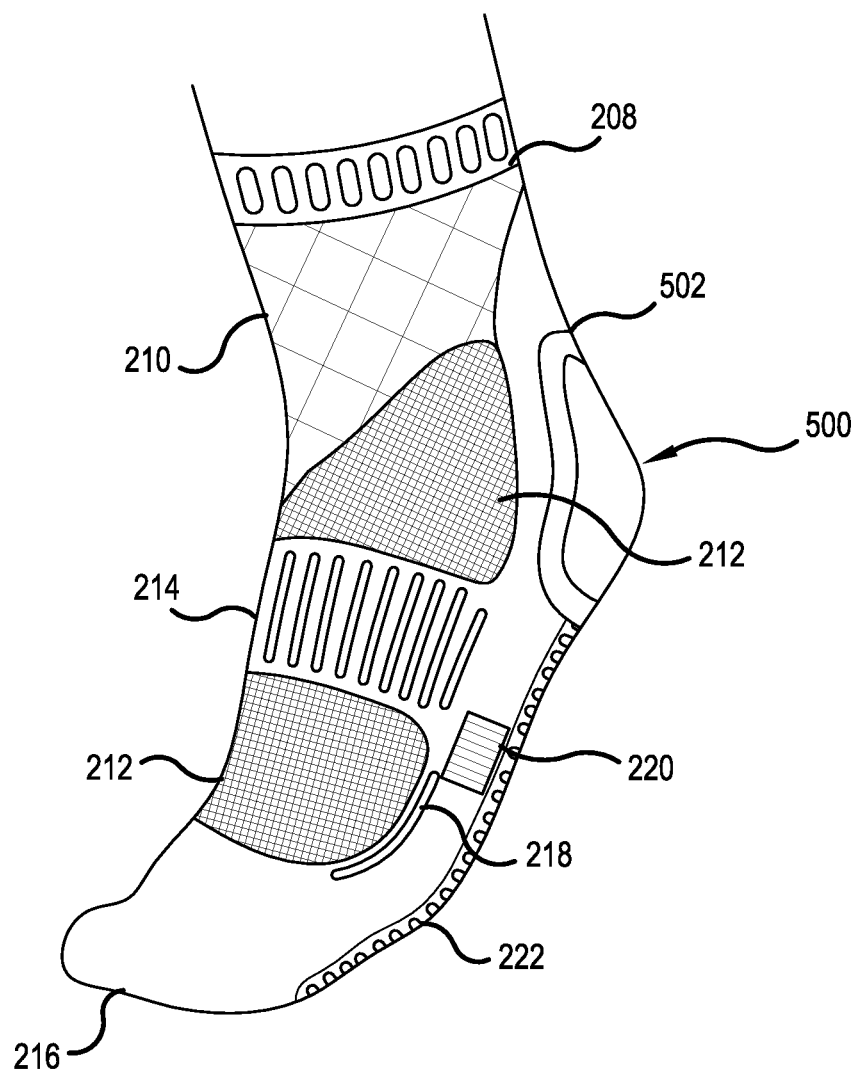
FIG. 3 illustrates a side view of the wound dressing garment of FIG. 2.

A second exemplary wound dressing garment similar to the sock 100 of FIG. 1 is illustrated in FIGS. 2 and 3. This sock shaped garment 200, hereinafter "sock" mostly differs from the sock 100 in that the sock 200 is a shorter length sock, often referred to as an ankle length sock, and the possible locations of the wound dressing 500. Based on the size of the sock 200, the wound dressing 500 is more generally localized around the heel and/or ankle of the individual and may cover the heel rim extending under the foot to the sole.

The sock 200 includes a foot portion 202 and an ankle portion 204. As shown in this exemplary embodiment, the wound dressing 500 may be located in the ankle portion 204; however, it is understood that the wound dressing 500 is not limited to this location. The wound dressing 500 includes a wound dressing border 502 that connects the wound dressing 500 to the sock 200. The wound dressing 500 will be discussed in greater detail below with respect to FIG. 6.

Figure 2A:
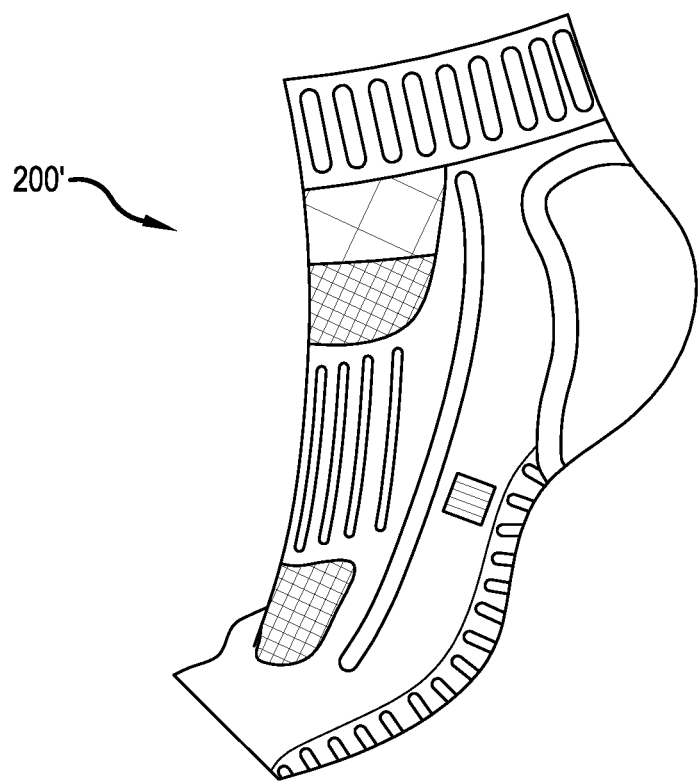

The sock 200 may include a non-binding, non-restrictive elastic cuff 208 provided at the top of the ankle portion 204. The cuff 208 may be attached to a large gauge mesh weave 210 that defines the upper portion of ankle portion 204 and is stretchable to allow a foot to be inserted through the opening of the sock 200 and to contract and collapse against the ankle of the individual once the foot is inserted. A smaller gauge mesh weave 212 is connected to the mesh weave 210 and spans the remaining ankle portion. The mesh weave 212 may be in the form of a panel so as to cover the dorsum of the foot and may extend upward as it tapers and is joined to the mesh weave 210. A non-wrinkle or non-cinching portion 214 may be provided in the middle of the mesh weave 212 or it can be provided at one end of the mesh weave 212 opposite the mesh weave 210. As shown in FIG. 2, the non-wrinkle portion 214 is located in a central region of the mesh weave 212 and the mesh weave 212 extends to a toe portion 216; however, it is understood that the non-wrinkle portion 214 may extend to the toe portion 216. The sock 200 ends at the toe portion 216 and the toe portion 216 may be designed to provide a wide or loose fit so as to not feel restrictive on a foot of the individual. To this end, the toe portion 216 may be seamless. Alternatively, the toe portion 216 may be eliminated, thereby providing an open-toe sock 200' arrangement as shown in FIG. 2A, so as to be less restrictive on the individual's foot.

The sock 200 may include a pair of evaporation channels 218 that extend along the sides of the sock from the toe portion 216 of the foot portion 202 towards the ankle portion 204. In addition, a pair of ventilation channel tabs 220, one for each side of the foot, may be disposed in the foot portion 202. The purpose of the evaporation channels 218 and ventilation channel tabs 220 is to allow for the evaporation and/or transportation of moisture.

A non-skid tread 222 may also be provided on the sole of the sock 200 in the foot portion 202. In the exemplary embodiment, the tread 222 extends between the ball of the foot and the heel of the foot; however, it is understood that the non-skid tread 222 may be provided at other portions of the sock. The tread 222 may be made of silicon rubber or other suitable materials.

Figure 4:
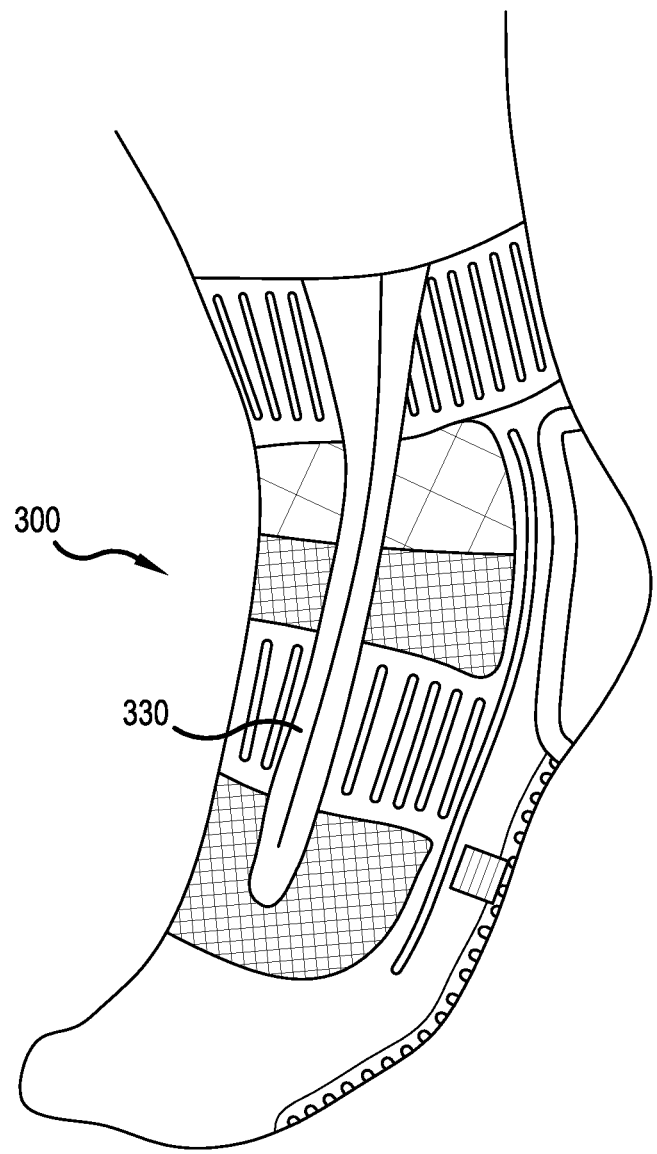
FIG. 4 illustrates a perspective view of a wound dressing garment according to a third exemplary embodiment of the present invention.

A third exemplary wound dressing garment similar to the sock 200 of FIGS. 2 and 3 is illustrated in FIG. 4. This sock shaped garment 300, hereinafter "sock" differs from the sock 200 in that the sock 300 is provided with a re-sealable opening 330. The purpose of the re-sealable opening is to allow positioning of the sock 300 on the individual without requiring that the sock be slid up the individual's foot. The re-sealable opening 330 may be in the shape of a V and can be closed using conventional means (not shown), such as, for example, VELCRO type tape or hook and loop fasteners, provided on opposing edges of the V shape opening. Other features of the sock 300 are similar to those described above regarding sock 200 and are not repeated here.

Figure 5:
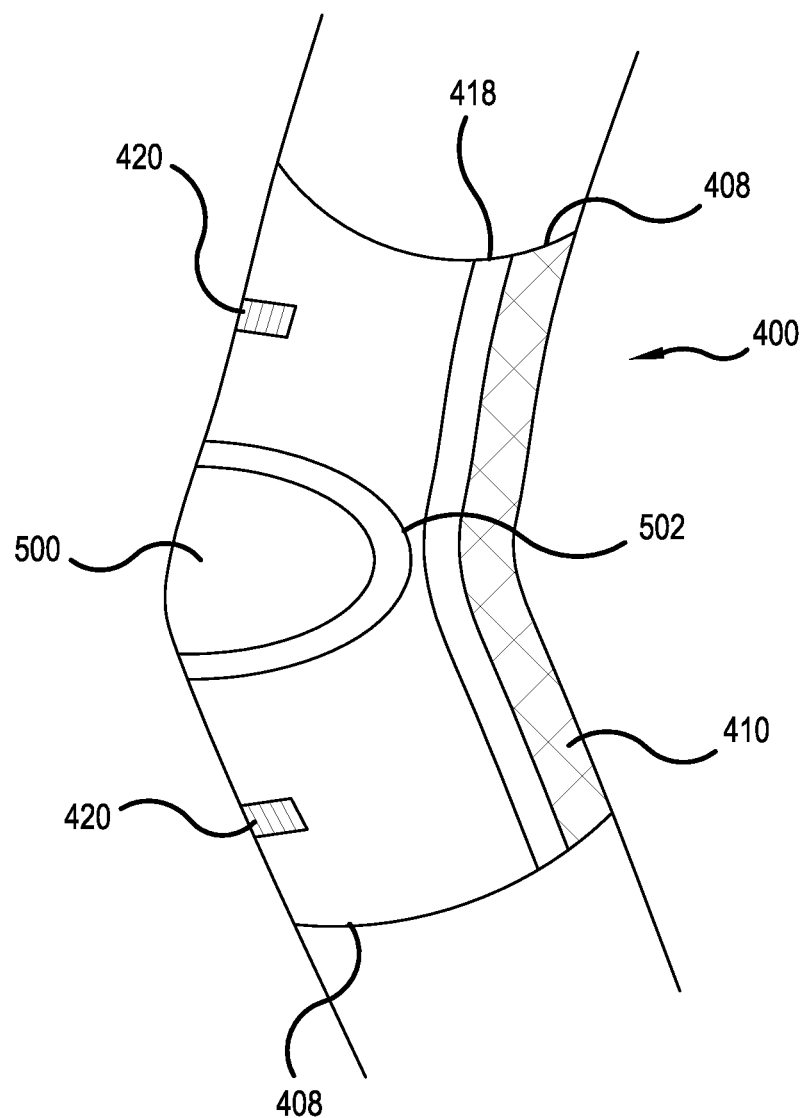
FIG. 5 illustrates a perspective view of a wound dressing garment according to a fourth exemplary embodiment.

Having described wound dressing garments that are in the form of sock shaped garments, it should be understood that the wound dressing garment is not limited to sock shape garments. A fourth exemplary wound dressing garment is illustrated in FIG. 5 as used on an appendage, in this case an arm. It is understood that this wound dressing garment could be used on the leg as well. The wound dressing garment includes a sleeve shaped garment 400, hereinafter "sleeve," and a wound dressing 500. The wound dressing 500 will be discussed in greater detail below with respect to FIG. 6.

Sleeve 400 includes a pair of non-binding, non-restrictive elastic cuffs 408 provided at opposite ends thereof. The cuffs 408 allow for the sleeve 400 to be easily positioned on an appendage to cover a joint, such as a knee or elbow, and to hold the sleeve 400 in place on the appendage. The sleeve 400 can include a wide band of non-binding, stretchable mesh material 410 that is connected to both cuffs 408. The mesh material 410 may be large gauge mesh that is easily stretchable to allow for the insertion of the appendage and to conform to the contour of the joint. In the case of an elbow, the mesh material 410 would be arranged in the crook of the arm. Preferably, the mesh material 410 would be selected so as not to overly wrinkle or bunch-up when the appendage is moved. As above, the wound dressing 500 may be affixed or attached to the sleeve 400 by a border 502.

The sleeve 400 may include a pair of evaporation channels 418 that extend along the length of the sleeve 400. In addition, a pair of ventilation channel tabs 420 are provided, one located on each side of the joint, which in this exemplary embodiment is the elbow. The purpose of the evaporation channels 418 and ventilation channel tabs 420 is to allow for the evaporation and/or transportation of moisture.

Similar to sock 300, the sleeve 400 may have a re-sealable closing strip (not shown). The purpose of the re-sealable closing strip is to allow positioning of the sleeve 400 on the individual without requiring that the sock be slid up the individual's appendage. The re-sealable closing strip may be any conventional means, such as, for example, VELCRO type tape or hook and loop fasteners, provided on opposing edges of the re-sealable closing strip.

To use the wound dressing garment, a health care professional or the individual can apply the sleeve 400 by sliding it in place over an appendage. Once in place, the wound dressing garment is arranged so that the wound dressing 500 may cover a knee, leg, elbow or arm to cover and/or treat any wounds, such as cuts, bruises, burns or ulcers or to prevent ulcers from forming in that area. The health care professional or individual can adjust the location of the wound dressing to cover a majority of wounds that could occur in these locations.

Figure 6:
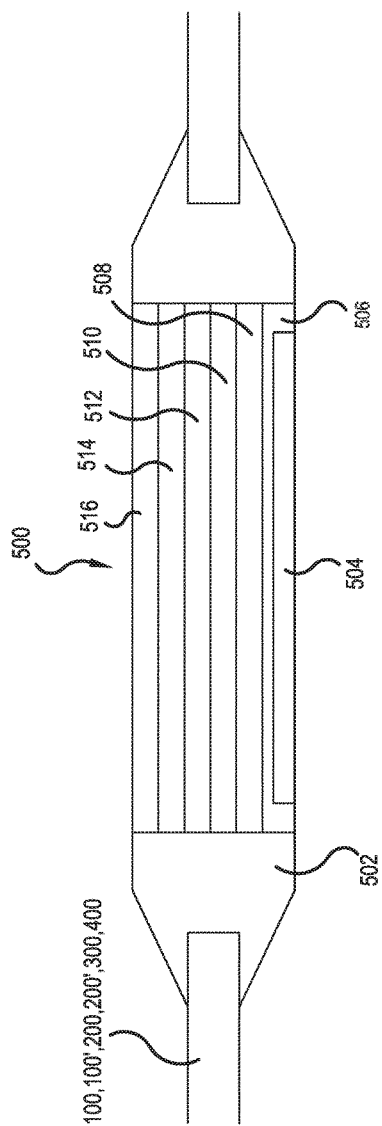
FIG. 6 is a schematic sectional view of an exemplary wound dressing affixed or attached to a garment.
Figure 7:
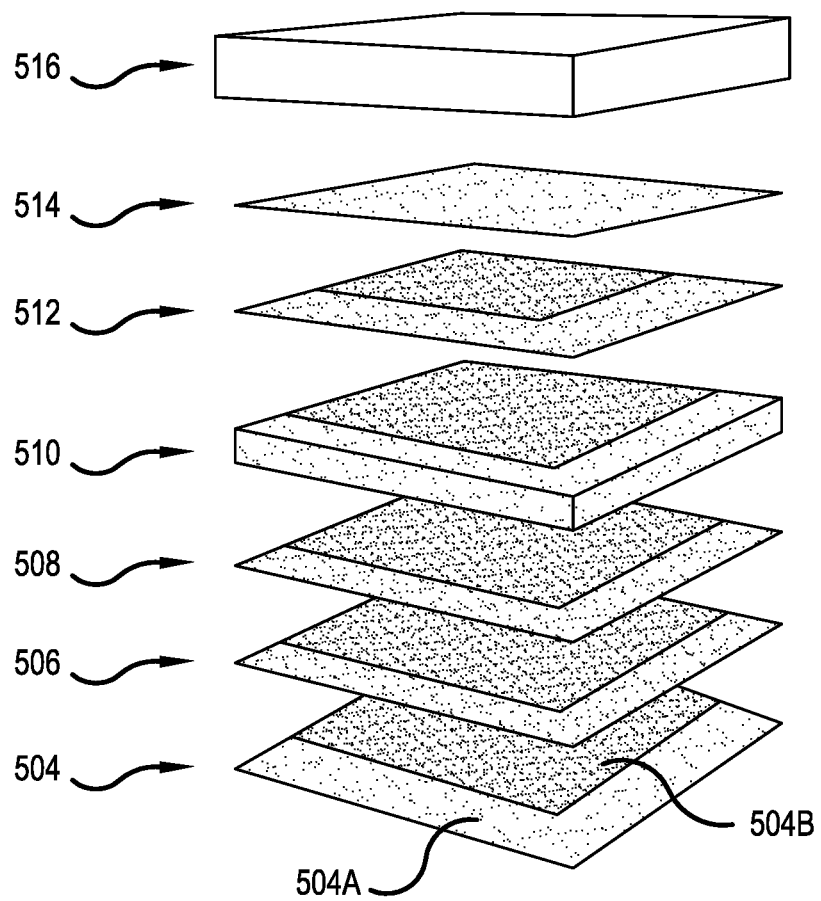
FIG. 7 illustrates an exploded perspective view of the exemplary wound dressing of FIG. 6.

Having described the various wound dressing garments, the wound dressing will be described with reference to FIGS. 6 and 7. As shown in FIG. 6, the wound dressing 500 may include a wound dressing border 502 that is connected to a sock 100, 100', 200, 200' or 300 or sleeve 400, a blister pack mesh layer 504, an adhesive layer 506, a hydrogel layer 508, a structural layer 510, a first transparent layer 512, a second transparent layer 514 and an outermost layer 516. The layers of wound dressing 500 may be arranged to provide a transparent portal to allow observation of the wound or potential wound area. It is understood that one or more of these layers may be excluded depending on the desired application of the wound dressing 500. The wound dressing 500 may have a bell shaped contour to cover an ankle or heel or may be a thin flexible panel to follow the contour of the body part where it is positioned.

The wound dressing border 502 surrounds the remaining layers of the wound dressing 500 and provides two functions. It secures the wound dressing 500 to the garment and provides structural integrity to the wound dressing 500. The border 502 is affixed or attached to the sock or sleeve via cold pressing, aqua sealing or other suitable manufacturing processes. For example, one method for affixing or attaching the border 502 to the sock or sleeve would involve providing a cut out portion in the sock or sleeve and sealing or adhering the cut out fringes of the sock or sleeve material between two spaced edges of the wound dressing border 502 so as to sandwich the cut out fringes between portions of the wound dressing border 502. In this manner, the wound dressing 500 may be reliably secured to the sock or sleeve.

The mesh layer 504 may be a sterile, perforated or semi-perforated layer that contacts the skin surrounding the wound area or potential wound area as well as extending over the area itself. For example, region 504a may be disposed around the wound area while region 504b covers the wound area. As shown, the mesh layer 504 does not need to extend all the way to the border 502 as it may be secured to the border 502 via the adhesive layer 506, although it is understood that different sized blister pack mesh layers could be provided. The mesh layer may be made of a material that is dissolvable or otherwise absorbable by the hydrogel in the hydrogel layer 508 once the hydrogel is dispersed.

The adhesive layer 506 is located between the mesh layer 504 and the hydrogel layer 508 and, as shown in the exemplary embodiment, may also be placeable into contact with the skin as it extends to the end of the border 502 to help hold the wound dressing 500 in place. The adhesive layer should be thin enough to allow the hydrogel layer to be activated through the mesh layer 504. The adhesive layer can be formed from any suitable adhesive and may also be a slightly tackier hydrogel composition than the hydrogel layer 508.

The hydrogel layer 508 is located above the adhesive layer and may be any suitable hydrogel or hydrogel in combination with antibiotics, anti-inflammatories and/or other medicinal aides. The appropriate amounts can be selected to provide desired results know to one of ordinary skill in the art. For example, as non-limiting examples, several different hydrogels are disclosed in U.S. Pat. No. 4,909,244 to Quarfoot et al. and U.S. Published Patent Application No. 2009/0148394 to Muno, which are incorporated herein by reference. An additional adhesive layer (not shown) may be provided between the hydrogel layer 508 and the mesh layer 504 that may attach the dispersed hydrogel to the skin once it has been exuded through the mesh layer.

The structural layer 510 is arranged above the hydrogel layer 508 and may be any suitable film material. The structural layer 510 may be stretchable so as to allow for expansion of the hydrogel layer if it absorbs wound exudate and to be flexible to allow the wound dressing 500 to follow the contours of region where the wound dressing 500 is placed on the body. Depending on the properties of the hydrogel layer and the structural layer 510 a bond may be provided by an intervening layer (not shown).

The first and second transparent layers 512 and 514 are provided to prevent the other layers from being easily separate from the border 502. The first and second layers may be selected from different materials to provide different properties. For example, the first transparent layer 512 may provide protection from outside bacteria and other contaminants. For example, it may be a hypoallergenic, non-adhesive flexible plastic film that allows vapor and gases to escape through the material in one direction but blocks contaminants and moisture from passing in the opposite direction.

The second transparent layer 514 may be the outermost layer from the skin and may be in the form of a thin, oxygen- and vapor-permeable film. The second transparent layer 514, in combination with the other layers may define a viewing portal such that the wound or potential wound area can be observed during treatment.

Outermost layer 516 may be optionally provided as a reinforcing layer to the transparent layers 512 and 514. In addition, outermost layer 516 may be selected from different materials from those of the transparent layers 512 and 514 depending on which additional properties are desired.

Once the wound dressing 500 has been assembled and attached to the garment, the wound dressing garment can be sealed in a sterile container or bag until it is to be used. At that point, the healthcare professional or individual simply removes the wound dressing garment and places it in position on the foot of the individual or appendage of the individual. Pressure can then be applied to the wound dressing 500 to activate it, which causes the hydrogel layer 508 to seep through or dissolve the mesh layer 504. After which, the wound dressing 500 can be monitored by the healthcare profession or individual.

The wound dressing garment assists in carrying out the treatment of wounds, ulcers or burns by providing a stable positioning of the hydrogel layer of the wound dressing. This position is assisted by the combination of the wound dressing with a lightweight garment, which may be a sock or sleeve. The wound dressing garment assists in application or positioning of the wound dressing, while diminishing or avoiding displacement of the dressing and may be expanded for use in treatment of other parts of the body. In certain circumstances, the patient can attend to his medication through the wound dressing directly without assistance from a healthcare professional. The placement and stability created through the securing of the wound dressings enables the advanced dressings to remain in place longer, aid in prevention of infection and promote healing.

The wound dressing garment provides advantages over other convention approaches in that the wound dressing garment can be provided as a unitary structure, which includes an adhesive border of the wound dressing for securing the wound dressing to the wound area, adding ease of application. The wound dressing garment also has the ability to contain exudates while providing vapor permeability. Additionally, the transparent wound dressing provides a hydrogel wound bed layer for resting the wound locus and thus reducing constant need for repositioning, while at the same time, providing a moist, cool climate for healing that can be easily monitored for effective treatment.

When the wound dressing garment is used to treat wounds, as opposed to protecting the skin from the generation of wounds, it can reduce one or more undesirable aspects of a wound. For example, in the context of a chronic skin lesion, the wound dressing garment can help in the reduction of pain associated with the wound, pain associated with the changing of the dressing, exudation, smell, irritation and/or hyperkeratosis.

The invention thus being described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A wound dressing garment comprising:
a wearable garment including a portion having a hole;
a wound dressing located in the hole, the wound dressing including:
   a border connecting the wound dressing to the wearable garment, the border extending around a perimeter of the hole to locate the wound dressing therein, the border defining a central opening;
   a hydrogel layer located at the central opening;
   a mesh layer disposed below the hydrogel layer, the mesh layer configured to allow dispersal of the hydrogel layer; and
   an adhesive layer to secure the mesh layer to the hydrogel layer and the border, the adhesive layer being located between the hydrogel layer and the mesh layer, the adhesive layer allowing the hydrogel layer to be activated through the mesh layer.

2. The wound dressing garment according to claim 1, wherein the wound dressing includes at least one transparent layer above the hydrogel layer.

3. The wound dressing garment according to claim 2, wherein the at least one transparent layer is formed of one of a hypoallergenic film, an oxygen-permeable film and a vapor-permeable film.

4. The wound dressing garment according to claim 2, wherein the at least one transparent layer includes a first transparent layer formed of a hypoallergenic film and a second transparent layer formed of an oxygen-permeable, vapor-permeable film.

5. The wound dressing garment according to claim 1, wherein the wound dressing includes a structural layer disposed above the hydrogel layer, the structural layer and adhesive layer preventing dispersion of the hydrogel layer prior to being placed on a body part.

6. The wound dressing garment according to claim 1, wherein the wearable garment is selected from one of a sock and a sleeve.

7. The wound dressing garment according to claim 1, wherein the wearable garment is a sock configured to be worn on a foot and the wound dressing is located in one of a heel region, an ankle region, and a leg region of the sock.

8. The wound dressing garment according to claim 1, wherein the wearable garment is a sleeve configured to be worn on an appendage and the wound dressing is locatable to cover a joint of the appendage.

9. The wound dressing garment according to claim 1, wherein the wearable garment includes at least one of a ventilation channel tab, an evaporation channel and a re-sealable opening.

10. The wound dressing garment according to claim 1, wherein the wearable garment is a sock having an elastic cuff and a non-cinching portion.

11. The wound dressing garment according to claim 1, wherein the wearable garment is a sleeve having a pair of elastic cuffs.

12. The wound dressing garment according to claim 1, wherein the hydrogel layer includes hydrogel in combination with antibiotics or anti-inflammatories.

13. A method of treating a wound on skin or preventing wound formation on skin, the method comprising:
   placing a wound dressing garment according to claim 1 on a foot or appendage;
   activating the wound dressing to cause dispersal of the hydrogel layer to the skin.

14. The method according to claim 13, further comprising monitoring the wound dressing.

15. The method according to claim 14, wherein monitoring the wound dressing includes observing the skin through the wound dressing.

* * * * *